United States Patent [19]

Mitchell et al.

[11] Patent Number: 5,084,680

[45] Date of Patent: Jan. 28, 1992

[54] DETECTION OF EXPOSED STEEL IN THE SURFACE OF REINFORCED CONCRETE

[75] Inventors: Thomas A. Mitchell, Mentor; John E. Bennett, Painesville, both of Ohio

[73] Assignee: Eltech Systems Corporation, Boca Raton, Fla.

[21] Appl. No.: 511,361

[22] Filed: Apr. 18, 1990

[51] Int. Cl.⁵ .................... G01Y 3/11; G01R 31/08
[52] U.S. Cl. ........................................... 324/559
[58] Field of Search ............... 324/557, 558, 559, 536

[56] References Cited

U.S. PATENT DOCUMENTS

| | | |
|---|---|---|
| 2,615,077 | 10/1952 | Tinker . |
| 2,920,270 | 1/1960 | Saw .................................. 324/557 |
| 3,284,789 | 11/1966 | Fisher . |
| 3,339,136 | 8/1967 | Rasor et al. . |
| 4,506,485 | 3/1985 | Apostolos . |

OTHER PUBLICATIONS

A publication entitled "Cathodic Protection of Reinforced Concrete Using Metallized Zinc", Materials Performance, vol. 26, Dec., 1987, pp. 22-28.
A Federal Highway Administration Report entitled "Further Improvements in Cathodic Protection of Bridge Structures", Report FHWA RD-87/062, dated Jun., 1987, pp. 8-10, 46-50.
A California Department of Transportation report dated May, 1989, entitled "Development, Testing and Field Application of Metallized Cathodic Protection Coatings on Reinforced Concrete Substructures", Report No. FHWA/CA/TL-89/04, pp. 31, 64, 69, 92, 93.

*Primary Examiner*—Walter E. Snow
*Attorney, Agent, or Firm*—John J. Freer

[57] ABSTRACT

A method for detecting exposed steel in the surface of reinforced concrete, comprising the steps of: moving an electrode across an exposed surface of said concrete; connecting said electrode to one terminal of a power source; connecting the other terminal of said power source to the reinforcement of said concrete; said power source providing a high voltage current effective to produce a spark across an air gap occurring when exposed steel is detected, said spark initiating a means to signal the occurrence of said exposed steel.

24 Claims, 3 Drawing Sheets

DETECTION OF EXPOSED STEEL IN THE SURFACE OF REINFORCED CONCRETE

BACKGROUND OF THE INVENTION

1. Technical Field

The present invention relates to cathodic protection systems for reinforced concrete structures, such as bridge and car park decks and piers. The present invention is particularly directed to locating exposed steel in the surface of the concrete. Such exposed steel can cause shorts in the cathodic protection systems.

2. Description of the Prior Art

In steel reinforced concrete structures, steel corrosion is the result of electrical current flowing from one point of the steel reinforcement to another. Such corrosion is enhanced by moisture and salt contamination of the concrete. Cathodic protection applies an external direct current to the steel reinforcement which counteracts the corrosive current.

U.S. Pat. No. 4,506,485 discloses one system for cathodic protection of reinforced concrete structures. The system comprises a coating of zinc metal which is flame-sprayed onto at least a part of the exposed concrete surface. The zinc metal coating is connected with the reinforcing steel through a power source by which current flow is induced from the metal coating to the reinforcing steel. By flame-spraying the metal onto the concrete, a coating is obtained which, in contrast to a metal coating painted onto the concrete and which contains a binder, is much more conductive. The flame-sprayed metal coating thus more effectively distributes the cathodic protection current to the reinforced concrete structure.

A publication entitled "Cathodic Protection of Reinforced Concrete Using Metallized Zinc", Materials Performance, Vol. 26, December, 1987, pages 22-28, discloses additional details of the system disclosed in U.S. Pat. No. 4,506,485.

A Federal Highway Administration Report entitled "Further Improvements in Cathodic Protection of Bridge Structures", Report FHWA RD-87/062, dated June, 1987, discloses subject matter closely related to the "Materials Performance" publication and to U.S. Pat. No. 4,506,485. On page 9 of the Report, it is confirmed that the zinc metallized coating has the advantage that it provides efficient current distribution. However, it is stated in the Report that the potential for electrical shorts, using a zinc metallized coating, is very high. These shorts are caused by exposed steel in the surface of the concrete. A short circuit can occur between the reinforcing steel and the metal coating. A short circuit can be caused by a tie wire for the reinforcing steel, used to tie the reinforcing bars together, having tie ends which extend into a crack in the concrete surface. A short circuit can also be caused by voids, such as cracks, crevices, potholes, or spalls in the concrete which expose a reinforcing bar or tie end. On page 49 of the Report, it is stated that prior to metal spraying, exposed steel should be located by visual inspection, and the surface scanned with a Fisher M-100 Rebar Locator. This is a magnetometer conventionally used to locate reinforcing steel. The magnetometer has a sensitivity which can be adjusted up or down. Because of the amount of steel in a conventional reinforced structure, the sensitivity of the magnetometer has to be turned down to the point where small wire ends from tie wires will not be detectable. On page 50 of the Report, reference is made to a test application in which, in a particular area, a total of eight shorts were found subsequent to metal spraying which were not located by visual inspection or use of a magnetometer. It is also indicated that these shorts were caused by protruding tie wire ends.

A California Department of Transportation report dated May, 1989 entitled "Development, Testing and Field Application of Metallized Cathodic Protection Coatings on Reinforced Concrete Substructures", Report No. FHWA/CA/TL-89/04, also discloses subject matter closely related to that of the "Materials Performance" publication and to U.S. Pat. No. 4,506,485. The report also confirms on page 93 that subsequent to sandblasting the concrete, the concrete should be electrically inspected to locate potential short circuits in the concrete.

SUMMARY OF THE INVENTION

The present invention resides broadly in a method and apparatus for detecting exposed steel in the surface of reinforced concrete. The method comprises moving an electrode across an exposed surface of the concrete. The electrode is connected to one terminal of a power source. The other terminal of the power source is connected to the reinforcement of the concrete. The power source provides a high voltage current which is effective to produce a spark across an air gap when the electrode is moved over exposed steel. The spark initiates a signal which indicates the existence of the exposed steel.

The apparatus of the present invention comprises an electrode; means for advancing said electrode across a surface of the reinforced concrete; a power source capable of providing a high voltage current; a lead connecting the power source with said electrode; a second lead connecting the power source with the reinforcement of said concrete; the voltage of said power source being effective to produce a spark across an air gap occurring when the electrode is moved over exposed steel; and means responsive to said spark for emitting a signal indicating the existence of the exposed steel.

Preferably, the power source is portable with said electrode and comprises a direct current battery of low voltage, a transformer and transistor in series to convert said low voltage to a pulsating high voltage, and a timer connected to said transistor to adjust the pulse characteristics of said pulsating high voltage.

The present invention also resides in a method for cathodic protection of reinforced concrete which comprises (a) thermally spraying a metal onto a surface of said concrete to form a layer of said metal on at least a part of said surface; and (b) connecting said layer of metal through a source of direct current with the reinforcement of said concrete, the improvement for detecting exposed steel in the electrical insulating characteristics of said reinforced concrete prior to said thermal spraying, comprising the steps of: moving an electrode across said surface; providing a power source having a high voltage current; connecting one terminal of said power source to said electrode; connecting the other terminal of said power source to the steel reinforcement of said concrete; the voltage of said power source being effective to produce a spark across an air gap occurring when said electrode is moved over exposed steel, said spark initiating a means to signal the occurrence of said exposed steel.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF PREFERRED EMBODIMENT

An electrical short circuit can occur between the steel reinforcement of concrete and a metal coating which is thermally sprayed onto the surface of the concrete. The short circuit can occur at any point where steel is exposed in the surface of the concrete. The exposure of steel can be caused by erosion of the reinforced concrete to the extent that a reinforcing bar is exposed, or more likely an end of a tie wire is exposed. An electrical short circuit can also occur at a "hot spot", which is more particularly discussed later hereinbelow. A "hot spot" exists where there is a covering of only a thin layer of concrete. The erosion can be in the form of a crack or a crevice into which molten thermally sprayed metal can flow, or in the form of a pothole or spalled area.

For purposes of the present application, the term "thermal-spraying" means any method for spraying molten metal onto a substrate, and includes such well-known processes as flame-spraying, arc spraying, and plasma spraying.

Figure 1:
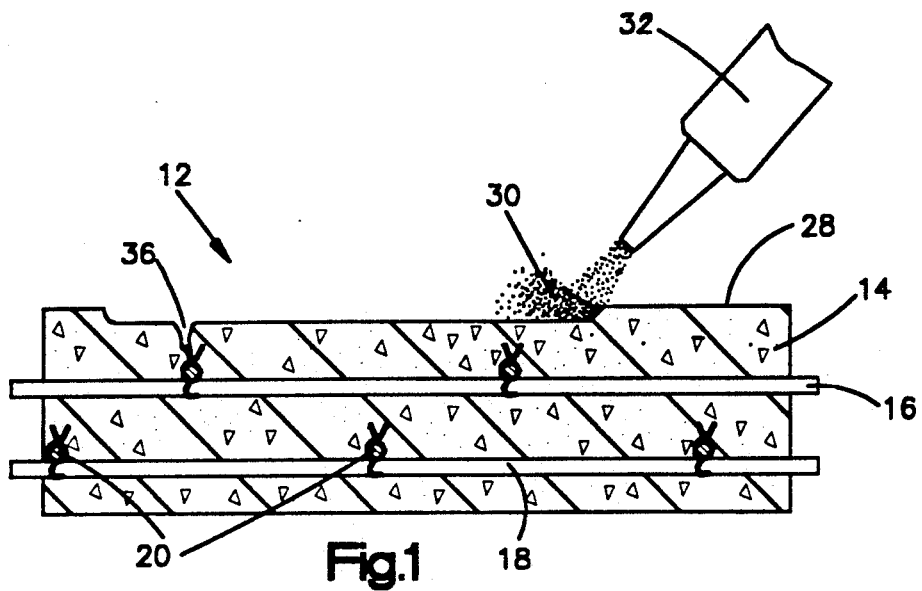
FIG. 1 is a diagrammatic view in cross-section showing the step of initially sandblasting the surface of reinforced concrete to prepare such surface.
Figure 1A:
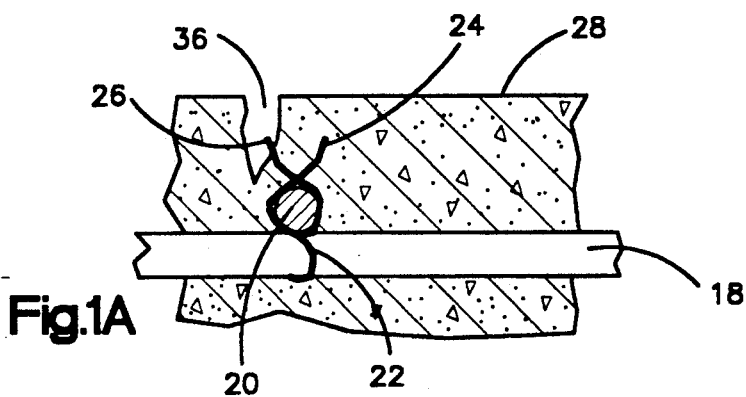
FIG. 1A is a diagrammatic enlarged view in cross-section showing a portion of the concrete of FIG. 1.

Referring to FIG. 1, a typical reinforced concrete structure 12 comprises a layer of concrete 14. At least one layer 16 of reinforcing steel is embedded in the concrete 14. Usually, a layer 16 of reinforcing steel comprises a series of bars 18 extending in one direction in the concrete 14, and a second series of bars 20 extending in a different direction, for instance at right angles to the bars 18. Frequently, the bars 18, 20 are connected together by tie wires 22, FIG. 1A. For convenience of installation of the reinforcement, the tie wire ends 24, 26 are coiled together on the top side of the bars 18, 20, with the ends 24, 26, FIG. 1A, protruding upwardly from the bars 18, 20 towards the surface 28 of the concrete.

In the process of preparing the reinforced concrete structure 14 for cathodic protection, the surface 28 of the concrete is first treated to remove any portion thereof which has been weathered and has deteriorated. This can be done by any conventional means. A preferred method is to eject a stream of grit or sand 30, FIG. 1, against the surface 28 using a sandblast gun 32. The concrete can be sufficiently weathered and decayed so that the sandblasting can expose areas of reinforcement. Usually, these areas of reinforcement can be detected visually, and the exposed areas can be readily patched. The sandblasting can also open up cracks and crevices, such as crevice 36, FIG. 1A, to expose tie wire end 26. If such crack or crevice 36 is very thin, the tie wire ends 24, 26, which are exposed, are not readily visible. When molten metal is applied to the prepared surface 28, for instance by flame spraying, the metal can flow into the crack or crevice 36 and establish a short circuit between the layer of molten metal and reinforcement.

Also of concern is a severely spalled area in which a tie wire end may extend close to the prepared surface, but be obscured from view by a thin layer of concrete. Current flow in a cathode protection system may be abnormally high through a thin layer of concrete creating a "hot spot". Such a hot spot is detrimental to the system causing undue wear on the anode and concrete at that location.

Figure 2:
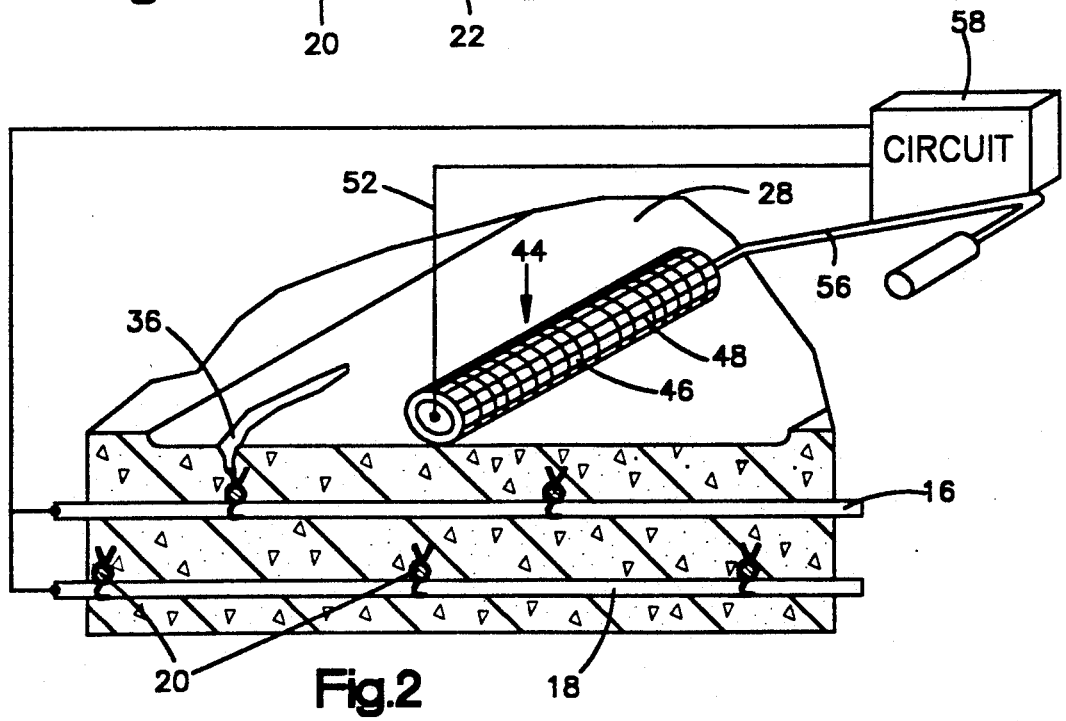
FIG. 2 is a diagrammatic view in cross-section showing the step of moving an electrode across the surface of said reinforced concrete to detect exposed steel in the surface of said concrete.

Referring to FIG. 2, subsequent to preparing the surface as in FIG. 1, but prior to application of molten metal to the surface, an electrode 44 is moved across the surface 28 to detect exposed steel in the surface of the reinforced concrete. Broadly, the electrode comprises a support and means on said support providing a plurality of contact points. The electrode in FIG. 2 preferably comprises a roller similar to a paint roller. The electrode 44 can also be a flat disk or coiled spring electrode, or wire brush, or can have any other convenient configuration. By way of example, the electrode 44 can have a concave face making it suitable for detecting exposed steel in a bridge column or other curved surface.

The electrode 44 in FIG. 2 comprises a nap or foamed electrically non-conductive substrate 46, which is somewhat deformable to accommodate irregularities in the prepared surface 28. A flexible, electrically conductive perforate wrap 48 is wrapped around and supported by the substrate 46. The perforate wrap 48 is connected to a wire lead 52 typically through a wiper contact end (not shown) electrically connected to the perforate wrap 48.

For the preferred roller electrode 44 there will be used an electrically non-conductive, preferably deformable roller electrode substrate 46. Advantageously for economy, such substrate 46 will be a polymeric substrate. Such substrate may be solid or for enhanced deformation may be foamed. Typical substrate materials include the thermoplastic polymeric materials such as polyethylene, polyurethane, polyester, and polypropylene polymers. The electrically conductive perforate wrap 48 around the roller electrode substrate 46 is generally a metal wrap 48 such as a metal wire mesh or screen. However, such may be a wire helically wrapped around the substrate 46. For the perforate wrap the metal employed may be steel, such as stainless steel, or other conductive metal such as titanium or metal alloy such as bronze.

A handle 56 extends upwardly from the roller 46. The handle supports a power source 58 which is connected by the lead 52 to the perforate wrap 48.

Figure 5:
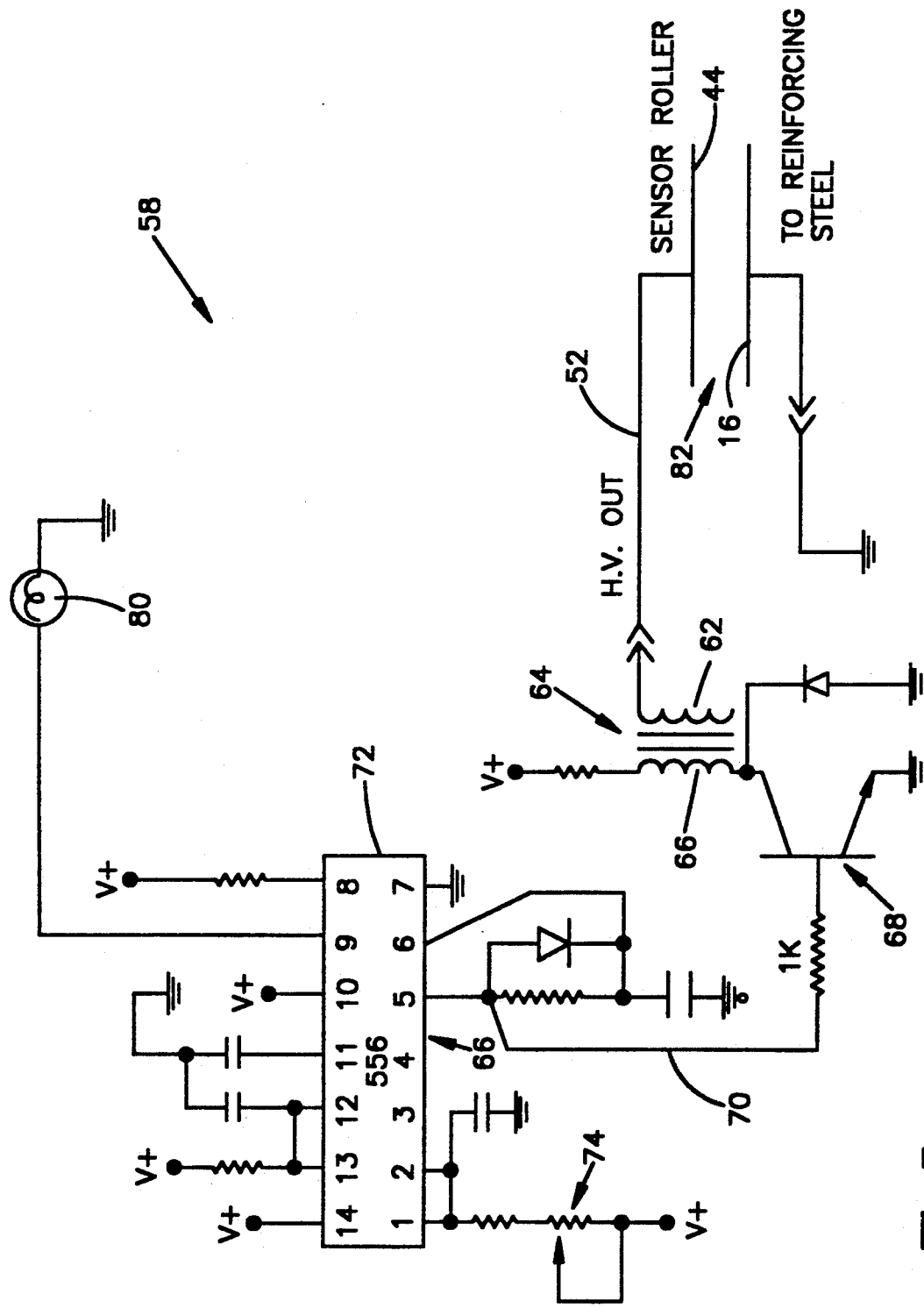
FIG. 5 is an electrical circuit useful with the electrode of FIG. 2.

Details of a suitable power source 58 are shown in FIG. 5. Power sources are known for obtaining a high, intermittent voltage from a source of low, steady voltage, such as a battery, for instance an automobile ignition system. In the system of FIG. 5, the lead 52 from the electrode ("sensor roller") 44 is connected to a secondary coil 62 of a transformer 64. The transformer 64 has a primary coil 66 which is coupled with the secondary coil 62. The primary coil 66 is connected in series with a transistor 68 to a low voltage, direct current source, such as a battery V+. The transistor 68 receives a pulse output in line 70 from the output pin 5 of a 556 integrated circuit timer 72. The integrated circuit timer 72 is made by a number of manufacturers. The timer 72, in this instance, was manufactured by Texas Instruments Company, Model No. NE556N. The timer 72 provides at pin 5 a series of pulses of fixed frequency, but of variable on time, or pulse width, controlled by control knob 74 of timer 72. Knob 74 controls primarily the on time pulse width. The pulse repetition rate is fixed. Each pulse in line 70 makes the transistor 68 conductive and completes a path for current flow from V+ through the primary coil 66 to the emitter circuit of transistor 68 to ground. The transformer 64 is configured so that with every make and break in the primary circuit coil 66, corresponding to the pulses in lead 70, an intermittent high voltage current is induced in lead 52. Varying the on-time pulse width of the timer 72 varies the output voltage of the coil 62. More voltage is obtained in lead 52 with greater pulse width, and less voltage with less pulse width. The timer 72 is also connected, at pin 9, with a warning device 80, such as a buzzer, horn or light. Both the reinforcing steel 16 and pin 8 of the timer 72 are connected to ground. In the event of exposed steel, a spark occurs across gap 82 between the electrode 44 and the reinforcing steel 16. This transmits a surge of current in pin 8 of the timer 72, which, in turn, activates the warning device 80. The warning device emits a signal to an operator that a discontinuity has been detected. By varying the output voltage of the coil, the spark jump distance can be varied. With more voltage, a greater spark jump distance is obtained. With less voltage, a smaller spark jump distance is obtained.

An advantage of the power source of FIG. 5 is that it is sufficiently compact and light weight that it can be mounted on the handle 56 of electrode 44 making the electrode assembly totally portable and free of any stationary power source and connecting wires. The battery V+ can be any compact six or twelve volt battery of light weight. The battery V+ preferably is rechargeable. Examples of suitable batteries are a nickel/cadmium or a lead/acid battery, weighing less than one pound.

However, it is contemplated, in accordance with the present invention that the electrode 44 can be used with a small portable or stationary generator if desired. Such generator can provide through a suitable transformer a high voltage alternating current which would be effective in locating exposed steel.

The amount of voltage required to detect a exposed steel can be varied depending upon the concrete structure being inspected and its environment. Generally, the voltage output will be above about 10,000 volts.

Figure 3:
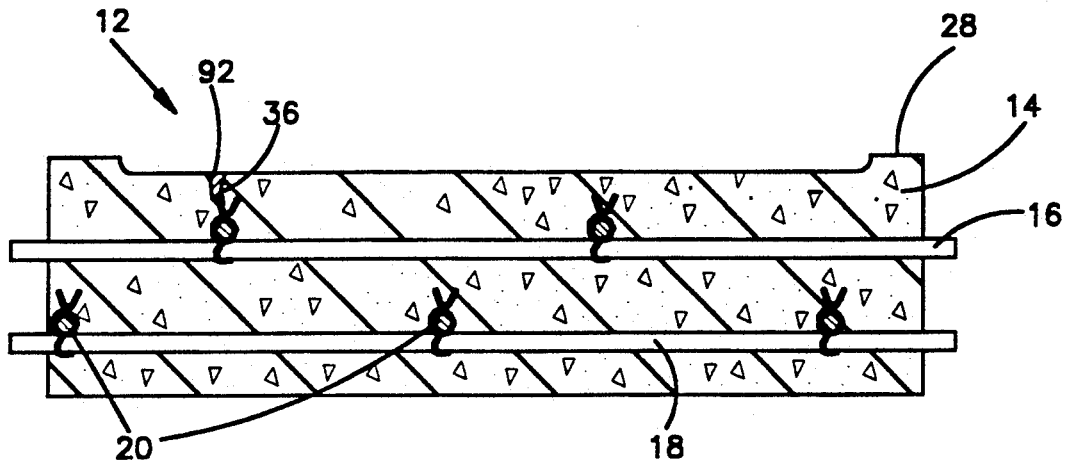
FIG. 3 is a diagrammatic view in cross-section showing the surface of said reinforced concrete repaired to eliminate the exposure of steel.
Figure 4:
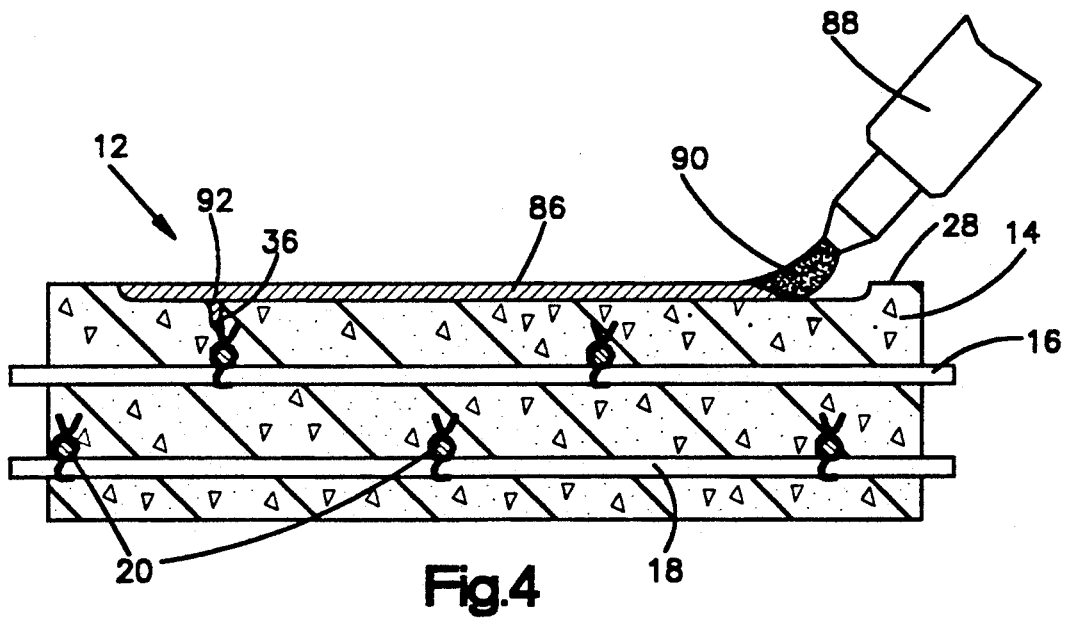
FIG. 4 is a diagrammatic view in cross-section showing the application of a metallic coating to the repaired surface of FIG. 3 by flame-spraying.

On detection of exposed steel, the cause for the exposed steel is located and the concrete is patched, for instance at crack or crevice 36, by patching 92, as shown in FIG. 3. After repair of the concrete, a protecting layer of molten metal 86 is then applied to the surface 28 of concrete 14, as shown in FIG. 4, following the procedure disclosed in U.S. Pat. No. 4,506,485. The molten metal can be any conductive metal. A preferred molten metal is zinc. The molten or liquified metal is discharged with substantial velocity from a conventional metallizing gun 88 which sprays the metal in finely divided particulate form 90 to provide a thermal deposit. The metallizing gun 88 can be any conventional thermal metallizing gun, such as a flame-spray mechanism, an arc sprayer, or a plasma spraying mechanism. The thermal spray mechanism is used so as to propel and deposit the metallic spray 90 in an evenly distributed layer. Being in molten form, it can enter and interchange with pits and depressions in the surface 28, but is prevented from doing so in crack 36 by patching 92. The metal can be laid down either as a sheet that is continuous, when cool and solid, or in discrete strips or areas, e.g., strips in a grid pattern, on the surface 28.

When the layer 86 has been completed, and solidified, it is connected through a source of direct current (not shown) to the reinforcing steel 16. This provides a flow of electrical current between the layer 86 and the reinforcing steel, by reason of the direct current source, which provides cathodic protection to the reinforcing steel 16. The disclosure of U.S. Pat. No. 4,506,485 is incorporated by reference herein.

From the above description of a preferred embodiment of the invention, those skilled in the art will perceive improvements, changes and modifications. Such improvements, changes and modifications within the skill of the art are intended to be covered by the appended claims.

Having described the invention, the following is claimed:

1. A method for detecting exposed steel in the surface of reinforced concrete, comprising the steps of:
   providing an electrode;
   moving said electrode across said surface of said concrete;
   connecting said electrode to one terminal of a power source;
   connecting the other terminal of said power source to the reinforcement of said concrete;
   said power source comprising an electrical circuit providing a high voltage current effective to produce a spark across an air gap occurring when said electrode is moved across exposed steel, said spark initiating a means to signal the occurrence of said exposed steel.

2. The method of claim 1 wherein said power source comprises a low-voltage, direct current battery, and said circuit comprises an induction coil means for transforming said low voltage, direct current to an induced high voltage intermittent current.

3. The method of claim 2 wherein said electrical circuit comprises a means for controlling the voltage of said induced current.

4. The method of claim 1 wherein said electrode comprises a support having a plurality of contact points.

5. The method of claim 2 wherein said induction coil is the coil of an automobile ignition system.

6. The method of claim 2 wherein the primary coil of said induction coil is connected in series with a transistor, said power source including means to provide a pulse input of variable frequency and pulse width to said transistor.

7. An apparatus for detecting exposed steel in the surface of reinforced concrete, comprising:
   an electrode;
   means for advancing said electrode across a surface of said concrete;
   a power source including an electrical circuit capable of providing a high voltage current;

a lead connecting said power source with said electrode;

a second lead connecting said power source with the reinforcement of said concrete;

said power source being effective to produce a spark across an air gap occurring when exposed steel is detected, said spark initiating a means to signal the occurrence of said exposed steel.

8. The apparatus of claim 7 wherein said power source comprises a source of low voltage direct current and said circuit comprises an induction coil for transforming said low voltage current to an induced high voltage intermittent current.

9. The apparatus of claim 8 wherein said electrical circuit comprises means for controlling the voltage of said induced current.

10. The apparatus of claim 8 wherein said electrode comprises a support having a plurality of contact points.

11. The apparatus of claim 8 wherein said power source includes an automobile ignition system coil.

12. The apparatus of claim 7 wherein said means for advancing said electrode across a surface includes a handle and said power source is mounted on said handle.

13. The apparatus of claim 12 wherein said apparatus comprises lightweight and readily portable unitary equipment.

14. In a method for cathodic protection of reinforced concrete which comprises:

(a) thermally spraying a metal onto a surface of said concrete to form a layer of said metal on at least a part of said surface; and (b) connecting said layer of metal through a source of direct current with the reinforcement of said concrete, the improvement for detecting exposed steel in the surface of said reinforced concrete prior to said thermal spraying, comprising the steps of:

moving an electrode across an exposed surface of said concrete;

connecting said electrode to one terminal of a power source;

connecting the other terminal of said power source to the reinforcement of said concrete;

said power source comprising an electrical circuit providing a high voltage current effective to produce a spark across an air gap occurring when exposed steel is detected, said spark initiating a means to signal the occurrence of said exposed steel.

15. The method of claim 14 wherein said power source comprises a low-voltage, direct current battery, and induction coil means for transforming said low voltage, direct current to a high voltage intermittent current.

16. The method of claim 15 wherein said power source comprises a means for controlling the voltage of said induced current.

17. The method of claim 14 wherein said electrode comprises a support having a plurality of contact points.

18. The method of claim 15 wherein said induction coil is the coil of an automobile ignition system.

19. An apparatus for detecting exposed steel in the surface of reinforced concrete, comprising:

an electrode;

means for advancing said electrode across a surface of said concrete;

a power source including an electrical circuit capable of providing a high voltage current; and a lead connecting said power source with said electrode;

said electrode comprising an inner, electrically nonconductive roller electrode substrate and an outer, electrically conductive perforate wrap;

said power source being effective to produce a spark across an air gap occurring when exposed steel is detected, said spark initiating a means to signal the occurrence of said exposed steel.

20. The apparatus of claim 19 wherein said inner roller substrate is a deformable, polymeric substrate.

21. The apparatus of claim 20 wherein said polymeric substrate comprises a polymer selected from the group consisting of polyethylene, polyurethane, polyester, polyvinylchloride and polypropylene polymers.

22. The apparatus of claim 19 wherein said outer perforate wrap is a metallic mesh or screen.

23. The apparatus of claim 22 wherein said metallic mesh or screen comprises stainless steel, titanium or bronze metal.

24. The apparatus of claim 19 wherein said roller electrode has a concave face.

* * * * *